United States Patent [19]

Ishida et al.

[11] Patent Number: 5,041,723
[45] Date of Patent: Aug. 20, 1991

[54] INFRARED RAY DETECTOR WITH MULTIPLE OPTICAL FILTERS

[75] Inventors: Masahiko Ishida; Toshikazu Ohnishi; Syuji Takada; Kimio Miyatake, all of Kyoto, Japan

[73] Assignee: Horiba, Ltd., Kyoto, Japan

[21] Appl. No.: 589,766

[22] Filed: Sep. 28, 1990

[30] Foreign Application Priority Data

Sep. 30, 1989 [JP] Japan .................................. 1-115430
Sep. 30, 1989 [JP] Japan .................................. 1-255539

[51] Int. Cl.$^5$ ............................................. G01N 21/61
[52] U.S. Cl. ..................................... 250/339; 250/343; 250/352
[58] Field of Search ............... 250/343, 339, 345, 346, 250/352

[56] References Cited

U.S. PATENT DOCUMENTS

| 4,678,914 | 7/1987 | Melrose et al. ................. 250/352 X |
| 4,771,176 | 9/1988 | Scheifer et al. ................. 250/343 X |
| 4,914,719 | 4/1990 | Conlon et al. ................. 250/343 X |

FOREIGN PATENT DOCUMENTS

| 5017276 | 2/1975 | Japan . |
| 604110 | 2/1985 | Japan . |
| 6448637 | 3/1989 | Japan . |

Primary Examiner—Carolyn E. Fields
Assistant Examiner—Drew A. Dunn
Attorney, Agent, or Firm—Joseph W. Price

[57] ABSTRACT

An infrared ray detector assembly for detecting a plurality of components such as hydrocarbons, $CO_2$ and CO gases includes a housing member having a hollow interior and a portion transmissible to infrared rays and a holder member mounted within the hollow interior and having a plurality of separate compartments. An infrared detector is mounted in each compartment, and an optical filter is mounted over each compartment, abutting adjacent filters to respectively limit the wavelength band to each infrared detector, each optical filter having a substrate of approximately the same material and thickness.

16 Claims, 4 Drawing Sheets

INFRARED RAY DETECTOR WITH MULTIPLE OPTICAL FILTERS

BACKGROUND OF THE INVENTION

1. Field of the Invention

The present invention relates to an improved infrared ray detector that can be used, for example, on an air-to-fuel ratio meter and the like and, more particularly, to an infrared ray detector assembly having an improved construction to remove noise while monitoring a plurality of wavelengths.

2. Description of the Prior Art

The prior art is aware of the need to monitor a plurality of components from a single source such as the exhaust of an automobile.

A selective infrared ray detector comprising a plurality of infrared ray detecting elements and a plurality of optical filters arranged corresponding to each respective infrared ray detecting elements has been disclosed in, for example, Japanese Patent Application Laid-Open No. Sho 50-17276. This detector is provided with three separate chambers, each having a concave section formed independently in a housing body. An infrared ray detecting element is arranged in each of the respective three chambers and optical filters for transmitting predetermined wavelength bands of infrared rays, corresponding to components to be measured, are inserted into entrance portions of the respective chambers and mounted on the housing of the infrared ray detector. In this infrared ray detector, the infrared rays, which have been transmitted through the respective optical filters, are incident upon the respective infrared ray detecting elements to provide output signals.

Spectral characteristics of the optical filters can be shifted to longer wavelengths with a temperature rise, and each of the respective optical filters can further have a different transmission wavelength band shifting. An infrared ray detector adapted to enable the regulation of the temperature of optical filters, in order to prevent such influences from affecting the performance of the optical filters, has been disclosed in Japanese Utility Model Publication No. Sho 60-4110. In this infrared ray detector, optical filters are arranged at respective end portions, which are separated from each other and stand side by side, of optical inlet ports to provide a V letter-shape in a metallic block while optical sensors are mounted on substrates arranged at the other end portions of the optical inlet ports. The metallic block is provided with a temperature sensor, and an endothermic-exothermic element is mounted on a side portion thereof at a distance from the optical filter and the optical sensor. The temperature of the metallic block is detected by the temperature sensor. The metallic block is subsequently cooled or heated by the endothermic-exothermic element on the basis of an output signal from the temperature sensor to regulate the temperature of the metallic block, thereby holding the optical sensor and the optical filter at a constant temperature.

An infrared ray detector provided with an infrared ray detecting element arranged in a cylindrical case has also been disclosed in Japanese Utility Model Application Laid-Open No. Sho 64-48637. In this infrared ray detector, a substrate is arranged in a cylindrical case formed of metal having an opening which is closed with a window material transmissible to an appointed wavelength band of infrared rays. A substrate is provided with an infrared ray detecting element mounted thereon. The infrared rays, which have been transmitted through the window material, are incident upon the infrared ray detecting element to provide an output signal.

An infrared ray detector disclosed in Japanese Patent Application Laid-Open No. Sho 50-17276 detects three separate components, but a disadvantage occurs in that its sensitivity is relatively low. In other words, the quantity of measuring signal is small.

An infrared ray detector disclosed in Japanese Utility Model Publication No. Sho 60-4110 is adapted to prevent any temperature change of the optical sensor and optical filter. The temperature change of the metallic block is detected and the temperature is regulated to hold the optical sensor and optical filter at a constant temperature. However, since there are differences in distance from the respective optical filters to the endothermic-exothermic element in view of the positional relationship between the endothermic-exothermic element provided on the metallic block and the two optical filters, it is difficult to regulate the temperature of both optical filters under the same condition. Thus, the temperature change of an optical filter distant from the endothermic-exothermic element is increased. In addition, since the optical sensor is mounted on the metallic sensor through the substrate, a time lag is also produced in the regulation of the optical sensor temperature.

In the infrared ray detector disclosed in Japanese Utility Model Application Laid-Open No. Sho 64-48637, the infrared ray detecting element is arranged to provide a window in an opening portion, but a side wall of the case is positioned around this infrared ray detecting element. Accordingly, the infrared rays, which have been transmitted through the window material are incident upon the inside of the case, and stray light, which has been incident upon an inner surface and the like of the case and reflected from there, are directly incident upon the infrared ray detecting element. Thus a problem can occur in that interference is apt to be produced with resulting noise in the output signals.

In the infrared ray detector disclosed in Japanese Patent Application Laid-Open No. Sho 50-17276, the entire optical filter is inserted into the entrance portion of three chambers, which are independently formed in the body of the infrared ray detector, respectively. Accordingly, a problem has occurred in that the cost of installing the respective optical filters is increased.

In addition, if the respective optical filters are placed in the entrance portion of the respective chambers, the optical filters can be easily installed. However, a problem can still occur in that light can leak from an end face of the optical filter, if it is not properly sealed, to produce interference.

Furthermore, if the respective substrates composing the respective optical filters are different in material, the processing procedures for the respective substrates are different depending upon the substrate conditions, such as the hardness of the respective material, so that the respective substrates can have a difference in thickness in many cases. Accordingly, if a plurality of substrates 21, 21' having different thicknesses are positioned side by side because of the difference in material, as shown in, for example, FIG. 7, step 22 is produced at the end faces of the substrates 21, 21'. If the infrared rays are incident upon the substrates 21, 21', a problem can occur in that light can leak from the step 22 to interfere with each filter.

SUMMARY OF THE INVENTION

The present invention solves the above-described problems, and it is an object of the present invention to provide a highly sensitive infrared ray detector capable of uniformly carrying out the regulation of the optical filters to remove the influence of temperature changes. The infrared ray detector is also capable of preventing the influences of stray light by reducing the possibility of the leakage of light into the housing.

The invention provides an infrared ray detector assembly, in which four infrared ray detecting elements are arranged with window materials transmissible to infrared rays in a sealed case. Respective optical filters, transmissible to infrared rays having respective wavelength bands absorbed by an HC gas, a $CO_2$ gas, a CO gas, and a standard reference gas, are arranged between the respective window materials and the respective infrared ray detecting elements. A design or central wavelength and a half-bandwidth of the wavelength band of infrared rays transmissible through the respective optical filters are set within a range of the following standard values, ±5%.

Optical filter for use in HC:
  Central wavelength: 3.4 $\mu$m;
  Half-bandwidth: 8.6%
Optical filter for use in $CO_2$:
  Central wavelength: 4.3 $\mu$m;
  Half-bandwidth: 4.2%
Optical filter for use in CO:
  Central wavelength: 4.7 $\mu$m;
  Half-bandwidth: 8.6%
Optical filter for use in the standard gas:
  Central wavelength: 3.8 $\mu$m;
  Half-bandwidth: 3.0% where the half-bandwidth value represents a percentage of the central wavelength.

The substrates for forming the respective optical filters have the same thickness and are adhered to each other at their respective end faces. The integrated respective filters are fixedly mounted on a holder in which the respective infrared ray detecting elements are further housed.

The substrates can be made of Si. In addition, a quantum type-, a pyroelectric-, a pyro-, and a thermopile infrared ray detecting element, such as PbSe, PbS, and InSb, and the like can be optionally used as the infrared ray detecting elements.

Within the housing member, a temperature regulating system is provided to compensate for any temperature changes. A support or holder is made of a highly heat conductive material for securing the optical filters. At the rear of the holder, a thermistor can be mounted for contacting the holder on one side and for being positioned on a thermal module such as a Peltier cooler unit which is, in turn, mounted directly onto a housing rear plate. The thermistor can monitor the actual temperature experienced by the holder which, in turn, is the temperature experienced by both the infrared detectors and the optical filters. The thermal module can be activated to control the temperatures at a predetermined value.

As can be appreciated, the holder is advantageously made of a metal material having, for example, a plurality of cavities or compartments for respectively mounting each of the infrared detectors. The holder can also advantageously hold the optical filters in a position adjacent and over each of the cavities. The holder in the temperature regulating system of the present invention is advantageously mounted on a rear plate which is, in turn, enclosed by a housing that extends over the holder and positions an entrance window above the optical filters.

The interior of the housing can be intentionally roughened to assist in the absorption of infrared rays. Additionally, blackened material can also be utilized to help eliminate reflections within the housing.

BRIEF DESCRIPTION OF THE DRAWINGS

The preferred embodiment of the present invention is shown in the drawings, in which.

DESCRIPTION OF THE PREFERRED EMBODIMENTS

Figure 1:
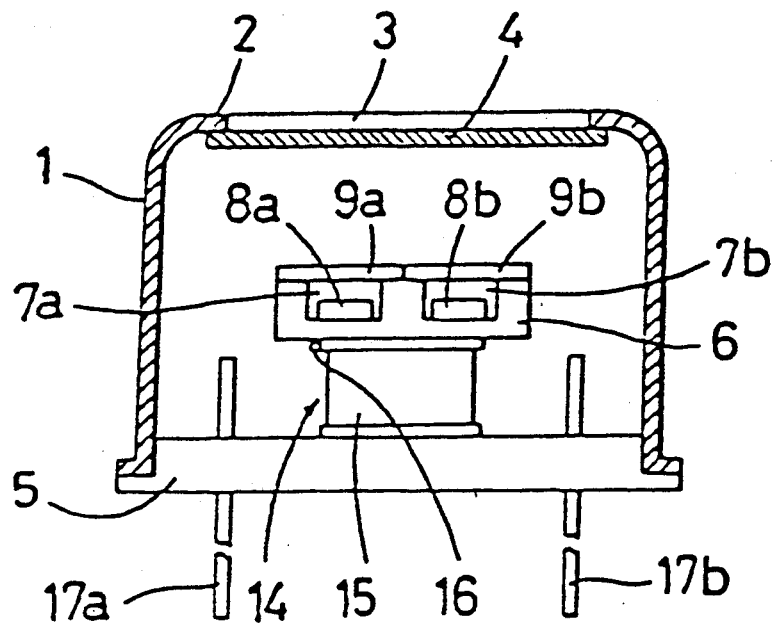
FIG. 1 is a sectional front view.
Figure 2:
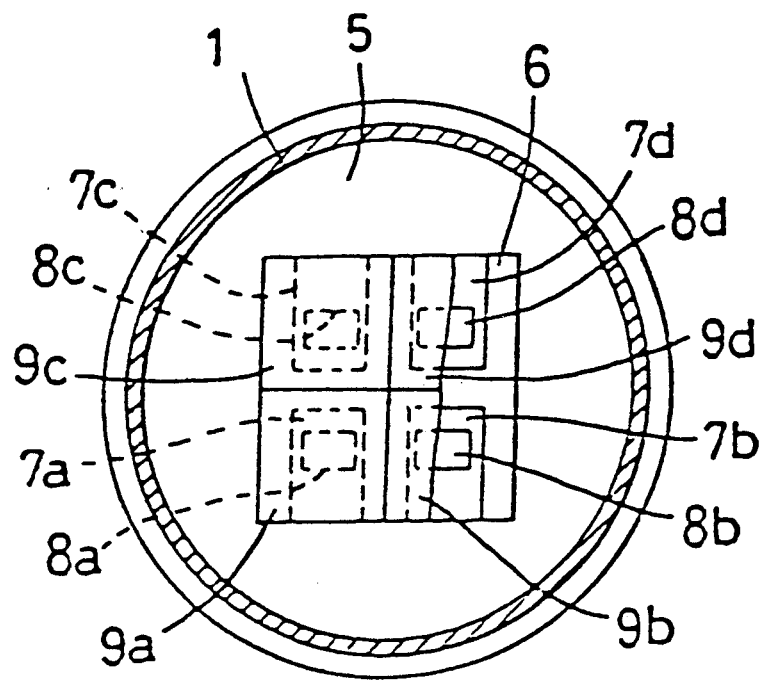
FIG. 2 is a partially cutaway sectional plan view showing an optical filter.

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein specifically to provide an improved infrared detector assembly.

Referring to the drawings, reference numeral 1 designates a cylindrical case or housing made of metal and the like. An opening portion 3 is formed on an end portion wall 2 of the case 1. The opening is closed with a window material 4, such as sapphire, which is transmissible to infrared rays. An inner surface of the case 1 is roughened, for example, by sandblasting. A blackening treatment can also be applied to the rough surface to absorb infrared rays. The case 1 is sealed by a rear plate 5, and $N_2$ or dry air is enclosed in the case 1 to prevent interior changes over a period of time.

Reference numeral 6 designates a support holder made of a highly heat conductive material, such as aluminum, which is arranged in the case 1 and positioned adjacent the window material 4. The holder 6 is provided with four separate rectangular groove-like housing portions or slots 7a, 7b, 7c, 7d with one end closed and the other end open. The respective housing portions 7a, 7b, 7c, 7d are provided with PbSe elements 8a, 8b, 8c, 8d as an infrared ray detecting element. The nitrogen charged into the case 1 will extend around the infrared detecting elements.

Reference numerals 9a, 9b, 9c, 9d designate, respectively, individual optical filters placed over the entrance portions of the housing portions 7a, 7b, 7c, 7d and mounted on the holder 6 for selecting separate wavelength bands of infrared rays incident upon a respective PbSe element 8a, 8b, 8c, 8d, the optical filter 9a being for HC, the optical filter 9b being for $CO_2$, the optical filter 9c being for CO, and the optical filter 9d being for a standard or reference gas.

Figure 3:
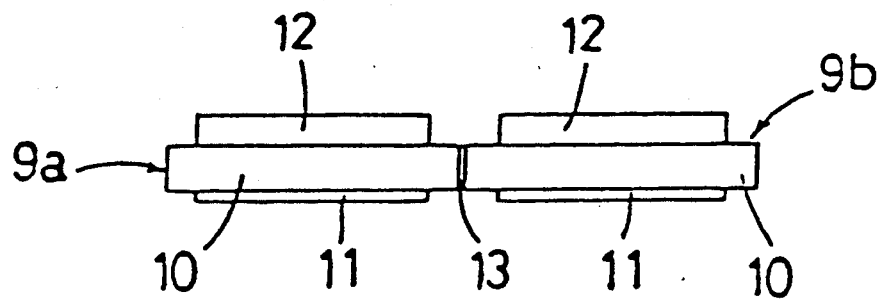
FIG. 3 is an enlarged front view showing an optical filter.
Figure 4:
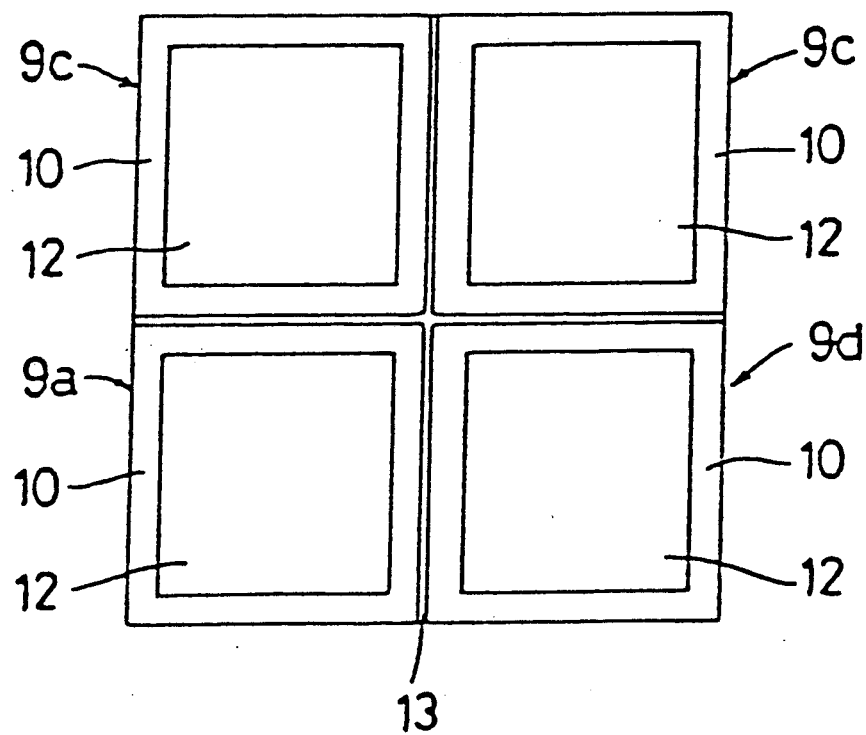
FIG. 4 is an enlarged plan view showing an optical filter.

In the optical filters 9a, 9b, 9c, 9d, as shown in FIGS. 3 and 4, a band-pass surface 11 (hereinafter referred to as BP surface) which is transmissible to an appointed wavelength band of infrared rays, depending upon the respective ingredients or components to be measured, is formed on one side of each substrate 10 which is made of Si and has the same thickness. A short-long wavelength cut surface 12 (hereinafter referred to as SLC surface) is provided for cutting a short wavelength band and a long wavelength band to remove any noise ingredients so that a predetermined transmission band is formed on the other side of the substrates 10. The BP surface 11 and the SLC surface 12 are formed of a multilayer film and the like, as known in the optical arts, and can be made of germanium (Ge) and silicon monoxide (SiO), respectively.

The design or central wavelength and a half-bandwidth of the respective wavelength bands of infrared rays transmissible through the respective optical filters 9a, 9b, 9c, 9d are set as follows:

Optical filter 9a for HC:
  Central wavelength: 3.4 $\mu$m;
  Half-bandwidth: 8.6%
Optical filter 9b for $CO_2$:
  Central wavelength: 4.3 $\mu$m;
  Half-bandwidth: 4.2%
Optical filter 9c for CO:
  Central wavelength: 4.7 $\mu$m;
  Half-bandwidth: 8.6%
Optical filter 9d for the standard gas:
  Central wavelength: 3.8 $\mu$m;
  Half-bandwidth: 3.0%

Figure 5:
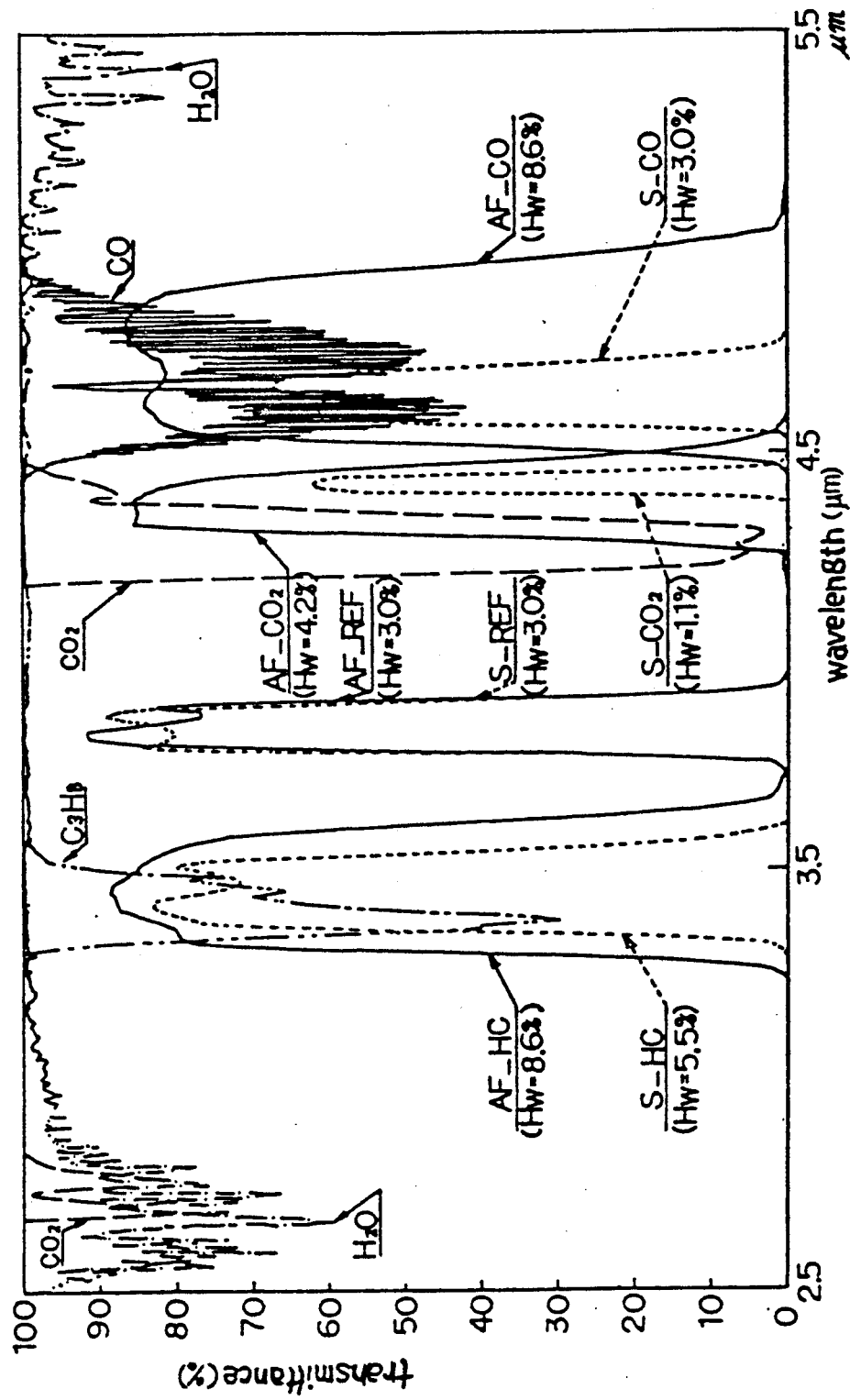
FIG. 5 is a diagram showing a relationship between an absorption spectrum of a sample gas and an optical filter.

Referring to FIG. 5, the value of a half-bandwidth can be calculated as follows for carbon dioxide. The peak amplitude of transmittance for a central wavelength of 4.3 $\mu$m is approximately 86%. One-half of that peak transmittance is 43%, and the width of the bandwidth at that position is about 0.18 $\mu$m. Thus the percentage of the half-bandwidth is obtained by dividing 0.18 $\mu$m by the central wavelength of 4.3 $\mu$m and multiplying the resultant quotient by 100.

$$0.18 \div 4.3 \times 100 = 4.2\%$$

The values of both the central wavelength and the half-bandwidth can vary by about 5%.

The optical filters 9a, 9b, 9c, 9d having the above-described construction are integrally adhered to each other with adhesives 13 adjacent end faces thereof so that the respective substrates 10 may form one continuous surface and can be closely adhered to the holder 6 with adhesives corresponding to the respective PbSe elements 8a, 8b, 8c, 8d, as shown in FIG. 3.

All the respective substrates of the optical filters can be made, for example, of Si or Ge, and can have the same thickness with relatively precisely cut end faces, so that they can be adhered to each other to, in effect, form one continuous surface. Such an arrangement not only prevents the leakage of light; it also facilitates in the mounting of the optical filters on the holder 6. The optical coatings that are formed on the respective filters can be produced by alternatively vapor coating a substrate with a material having a high refractive index and, subsequently, with a material having a low refractive index, to provide a multilayer optical coating, as known in the optical arts. A single substrate can have a plurality of optical filters arranged, and then subsequently cut to form the individual optical filters. Since preferably the substrates are all formed of the same material and have the same thicknesses, their respective expansion coefficient and thermal conductivity will be uniform, thereby assisting in the regulation of the effects of temperature on the respective optical filters.

Reference numeral 14 in FIG. 1 designates a temperature-regulating system which includes a thermomodule 15, such as a Peltier effect cooler, mounted on the plate 5 and a thermistor 16 overlapped on one end of the thermomodule 15. The thermistors 16 are mounted on surfaces facing the optical filters 9a, 9b, 9c, 9d of the holder 6. Reference numerals 17a, 17b designate lead pins passing through the rear plate 5. The connection of lead wires with the lead pins 17a, 17b are not shown.

In the infrared ray detector having the abovedescribed construction, the infrared rays, which have been transmitted through the window materials 4, are selectively transmit through the respective optical filters 9a, 9b, 9c, 9d to be incident upon the respective PbSe elements 8a, 8b, 8c, 8d, thereby simultaneously and separately detecting the respective infrared rays.

When PbSe elements 8a, 8b, 8c, 8d are used as the infrared ray detecting sensor in this infrared ray detector, the temperature of the PbSe elements 8a, 8b, 8c, 8d is held almost constant through the use of the heat conductive holder 6 by means of the thermistor 16 and the thermomodule 15, so that the infrared rays can be detected with high selectivity.

FIG. 5 shows a relationship between the absorption spectrums of the respective gases to be monitored and the optical filters 9a, 9b, 9c, 9d. In addition, the respective optical filters for HC, $CO_2$, CO, and the standard gas, which have been conventionally used, are also described for comparison. Accordingly, the optical filters 9a, 9b, 9c, 9d in this preferred embodiment are shown by adding AF before the respective ingredients to be measured. The standard gas (shown by REF) and the conventional respective optical filters are shown by adding S before the respective ingredients to be measured and the standard gas (shown by REF).

As obvious from FIG. 5, both the central wavelength and the half-bandwidth of the wavelength band transmissible through the optical filter 9a for the standard gas are almost the same as those of the conventional optical filter. However, the half-bandwidths of the other optical filters 9b, 9c, 9d are set at values considerably larger than those of the conventional optical filter.

These respective central wavelengths and half-bandwidths have been found to achieve an improvement in the detector sensitivity. The setting of the central wavelengths and the half-bandwidths of the optical filters 9a, 9b, 9c, 9d in the above-described manner has led to an increase in the quantity of measuring signal and, thus, to the possibility of detecting the respective infrared rays with high sensitivity. A highly sensitive infrared ray detector exhibiting a high-speed response and high selectivity with less noise can be obtained by using PbSe elements 8a, 8b, 8c, 8d as the infrared ray detecting element in this preferred embodiment.

Since three ingredients, HC, $CO_2$, and CO, can be simultaneously detected with high selectivity and high sensitivity, the infrared ray detector according to the present invention can be used as, for example, an air-to-fuel ratio meter exhibiting a high-speed response for automotive applications.

Although PbSe is used as the infrared ray detecting element in this preferred embodiment because of the high-speed response of PbSe, it is also possible that a pyrosensor and the like can be used as the infrared ray detecting element.

As described above, in this infrared ray detector, all of the substrates 10 composing the respective optical filters 9a, 9b, 9c, 9d have the same thickness and are adhered to each other at their respective end faces thereof to form one continuous plate, as shown in FIG. 3, to minimize the possibility that infrared rays will be leaked from the respective adhered end faces of the substrates 10 when the infrared rays are incident upon the optical filters 9a, 9b, 9c, 9d. Thus, noise interference can be avoided. In addition, since four pieces of optical filter 9a, 9b, 9c, 9d are arranged on one surface, they can be easily mounted on the holder 6 without forming gaps. It is also possible to prevent the leakage of light from the surface at the positions where the optical filters 9a, 9b, 9c, 9d are mounted on the holder 6.

If all of the substrates 10 are made of the same material, such as Si, the manufacturing conditions of the respective substrates 10 and the like are the same, so that the thicknesses of all of the substrates 10 can be easily equalized. In addition, in the case of Si, custom cutting of the plates is relatively easy, and the quantity of chippings produced by this cutting can be reduced. In addition, the size of the chippings produced is relatively small. Thus, the possibility is increased of preventing the leakage of light from the adhered end faces of the respective substrates 10 when they are adhered to each other. Other material, such as Ge, which is transmissible to infrared rays, can also be used for forming the substrates 10.

In this infrared ray detector, PbSe elements 8a, 8b, 8c, 8d are housed in the housing portion 7a, 7b, 7c, 7d of the holder 6 made of a highly heat-conductive material such as aluminum. The optical filters 9a, 9b, 9c, 9d directly contact and are mounted on the holder 6, with the temperature-regulating system 14 being mounted on a side opposite to the optical filters 9a, 9b, 9c, 9d of the holder 6. After the temperature of the holder 6 is detected by the thermistor 16, the holder 6 is regulated to an appointed temperature by means of the thermomodule 15, depending upon the detected temperature. Thus, the temperature of the holder 6 can be almost uniformly and effectively regulated. Also, the temperature of each of the PbSe elements 8a, 8b, 8c, 8d can be held constant. Moreover, since the optical filters 9a, 9b, 9c, 9d are mounted on the surface adjacent to the temperature-regulating system 14 of the holder 6, the heat conductance between the holder 6 and the optical filters 9a, 9b, 9c, 9d can be smoothly carried out, and the distances from all of the optical filters 9a, 9b, 9c, 9d to the corresponding temperature-regulating system 14 are almost equal. It is thus possible for all of the optical filters 9a, 9b, 9c, 9d to be uniformly regulated to hold them at a constant temperature.

As described above, since all of the optical filters 9a, 9b, 9c, 9d can be uniformly held at a constant temperature, it is possible to prevent a shift of their spectral characteristics to longer wavelengths due to changes in temperature. In addition, since the optical filters 9a, 9b, 9c, 9d are uniformly transmissible to the appointed wavelength bands of infrared areas specified for them, infrared rays can be detected with high selectivity and high sensitivity, and any interference factor can be reduced.

Moreover, if all of the optical filters 9a, 9b, 9c, 9d are made of the same material, such as Si, and integrally adhered to each other at the end faces thereof, the expansion coefficient and the thermal conductivity of the respective substrates 10 are made uniform. Thus, the temperature characteristics are improved. Accordingly, the temperature-regulation of the optical filters 9a, 9b, 9c, 9d through the holder 6 can be more effectively and uniformly achieved. Thus all of the optical filters 9a, 9b, 9c, 9d can be held at a constant temperature.

In addition, although the infrared ray detector provided with four PbSe elements 8a, 8b, 8c, 8d and four optical filters 9a, 9b, 9c, 9d was described in this preferred embodiment, the optical filters can be held at a constant temperature even though the number of infrared ray detecting elements and optical filters is smaller than four.

Even though the infrared rays, which have been transmitted through the window materials 4, are incident upon the inside of the case 1 and can become stray light, they would be reflected by the side surfaces of the holder 6 and not be incident upon the PbSe elements, 8a, 8b, 8c, 8d, thereby avoiding any interference. Additionally, the coloring of the holder 6 in black will further absorb stray light incident upon the holder 6.

If the inner surface of the case 1 is first roughened by sandblasting, the blackening treatment on the roughened surface or the like will also absorb the infrared rays without reflecting them.

Figure 6:
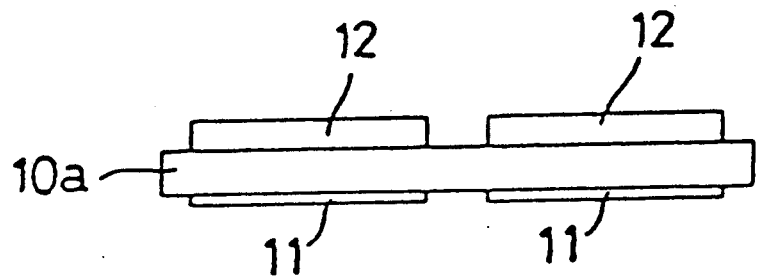
FIG. 6 is an enlarged front view showing an optical filter comprising one piece of substrate.
Figure 7:
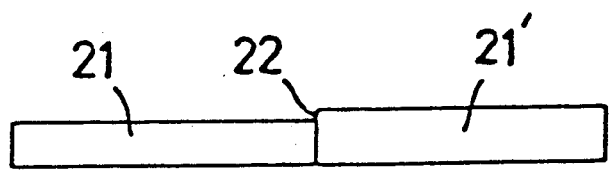
FIG. 7 is an enlarged front view showing a substrate with steps at an end face.

If a filter substrate 10a made of, for example, Si is provided with a required number of BP surface 11 and SLC surfaces, respectively, as shown in FIG. 6, the problem of the steps brought about in the case where a plurality of substrates 10 are adhered to each other and the like can be easily solved. However, the number of multilayer films composing the respective BP surfaces 11 and the respective SLC surfaces 12 can be different due to the difference in wavelength band of the infrared rays to be transmitted. Accordingly, the formation of the BP surfaces 11 and the SLC surfaces 12 can be difficult, but the optical filter shown in FIG. 6 can be effective if these problems can be solved on a commercial basis.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. An infrared ray detector assembly for detecting a plurality of components, including HC, $CO_2$, and CO, comprising:

a holder member;
infrared detectors mounted on the holder member corresponding to each component to be detected;
optical filters mounted across each infrared detector having a design wavelength and a half-bandwidth as follows:

Optical filter for use in HC:
 Central wavelength: 3.4 $\mu$m;
 Half-bandwidth: 8.6%
Optical filter for use in $CO_2$:
 Central wavelength: 4.3 $\mu$m;
 Half-bandwidth: 4.2%
Optical filter for use in CO:
 Central wavelength: 4.7 $\mu$m;

Half-bandwidth: 8.6%
Optical filter for use in the standard gas:
   Central wavelength: 3.8 μm;
   Half-bandwidth: 3.0%
wherein each half-bandwidth value represents a percentage of the associated central design wavelength and can vary by ±5%.

2. The invention of claim 1 wherein each optical filter has a substrate of the same thickness, each adhered together to provide a continuous surface.

3. The invention of claim 1 further including means for regulating the temperature of the optical filters.

4. The invention of claim 1 wherein the holder member includes a series of slots, each slot supporting a different infrared detector.

5. The invention of claim 1 further including a housing member extending over the holder member, the housing member having an inner surface roughened to absorb infrared rays.

6. The invention of claim 2 wherein each substrate is formed of a material consisting of one of Si or Ge.

7. The invention of claim 3 wherein the temperature regulating means includes a thermomodule and a thermistor, the thermistor mounted on the holder member and overlapping one end of the thermomodule.

8. An infrared ray detector as set forth in claim 2, wherein all substrates composing the respective optical filters are made of Si.

9. An infrared ray detector assembly for detecting a plurality of components in automotive exhaust gases, comprising:
   a housing member having a hollow interior and a portion transmissible to infrared rays;
   a holder member mounted within the hollow interior and having a plurality of separate compartments;
   an infrared detector mounted in each compartment, and
   an optical filter mounted over each compartment to respectively limit the wavelength band to each infrared detector, each optical filter having a substrate of approximately the same thickness and abutting an optical filter extending over an adjacent compartment.

10. The invention of claim 9 wherein the optical filters have a design wavelength and a half-bandwidth as follows:
Optical filter for use in HC:
   Design wavelength: 3.4 μm;
   Half-bandwidth: 8.6%
Optical filter for use in $CO_2$:
   Design wavelength: 4.3 μm;
   Half-bandwidth: 4.2%
Optical filter for use in CO:
   Design wavelength: 4.7 μm;
   Half-bandwidth: 8.6%
Optical filter for use in the standard gas:
   Design wavelength: 3.8 μm;
   Half-bandwidth: 3.0%
wherein each half-bandwidth value represents a percentage of the associated design wavelength at one-half of the peak transmittance and can vary by ±5%.

11. The invention of claim 9 further including means for regulating the temperature of the optical filters.

12. The invention of claim 9 wherein the housing member has an inner surface roughened to absorb infrared rays.

13. The invention of claim 9 wherein each substrate is formed of a material consisting of one of Si or Ge.

14. The invention of claim 11 wherein the temperature regulating means includes a thermomodule and a thermistor, the thermistor mounted on the holder member and overlapping one end of the thermomodule.

15. In an infrared ray detector, in which four infrared ray detecting elements are arranged to receive infrared rays through a window in a sealed case, the improvement comprising:
   respective optical filters transmissible to infrared rays having respective wavelength bands absorbed by an HC gas, a $CO_2$ gas, a CO gas, and a standard gas are arranged between the respective windows and said respective infrared ray detecting elements;
   a central wavelength and a half-bandwidth of said wavelength bands of infrared rays transmissible through the respective optical filters and set within a range of the following standard values ±5%:
Optical filter for use in HC:
   Central wavelength: 3.4 μm;
   Half-bandwidth: 8.6%
Optical filter for use in $CO_2$:
   Central wavelength: 4.3 μm;
   Half-bandwidth: 4.2%
Optical filter for use in CO:
   Central wavelength: 4.7 μm;
   Half-bandwidth: 8.6%
Optical filter for use in the standard gas:
   Central wavelength: 3.8 μm;
   Half-bandwidth: 3.0%
wherein each half-bandwidth value represents a percentage of the associated central wavelength at one-half of the peak transmittance.

16. An infrared ray detector as set forth in claim 15, wherein all substrates of said respective optical filters have the same thickness and are adhered to each other at respective end faces, to form one continuous surface, and said respective optical filters are fixedly mounted on a holder in which the respective infrared ray detecting elements are housed.

* * * * *